United States Patent
Lu et al.

(10) Patent No.: US 11,033,482 B2
(45) Date of Patent: Jun. 15, 2021

(54) REMOVABLE COATING SYSTEMS AND METHODS

(71) Applicant: Arkema France, Colombes (FR)

(72) Inventors: Jin Lu, West Chester, PA (US); Jinping Wu, Exton, PA (US); Xiaoxing Dong, West Chester, PA (US)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 15/524,048

(22) PCT Filed: Nov. 6, 2015

(86) PCT No.: PCT/EP2015/075970
§ 371 (c)(1),
(2) Date: May 3, 2017

(87) PCT Pub. No.: WO2016/071510
PCT Pub. Date: May 12, 2016

(65) Prior Publication Data
US 2017/0333334 A1    Nov. 23, 2017

Related U.S. Application Data

(60) Provisional application No. 62/076,706, filed on Nov. 7, 2014.

(51) Int. Cl.
| | | |
|---|---|---|
| *A61K 8/91* | (2006.01) | |
| *A61Q 3/02* | (2006.01) | |
| *C08G 18/67* | (2006.01) | |
| *C08G 18/22* | (2006.01) | |
| *C08G 18/75* | (2006.01) | |
| *C09D 175/16* | (2006.01) | |
| *C08G 18/42* | (2006.01) | |
| *A61K 8/87* | (2006.01) | |
| *A61K 8/35* | (2006.01) | |
| *C08F 290/06* | (2006.01) | |

(52) U.S. Cl.
CPC ............... *A61K 8/91* (2013.01); *A61K 8/35* (2013.01); *A61K 8/87* (2013.01); *A61Q 3/02* (2013.01); *C08F 290/067* (2013.01); *C08G 18/227* (2013.01); *C08G 18/4238* (2013.01); *C08G 18/672* (2013.01); *C08G 18/755* (2013.01); *C09D 175/16* (2013.01); *A61K 2800/81* (2013.01); *A61K 2800/95* (2013.01)

(58) Field of Classification Search
CPC ........ A61Q 3/02; A61K 2800/95; A61K 8/87; A61K 8/91; C08G 18/755
See application file for complete search history.

(56) References Cited

U.S. PATENT DOCUMENTS

| | | |
|---|---|---|
| 5,965,147 A | 10/1999 | Steffier |
| 6,391,938 B1 | 5/2002 | Lilley |
| 6,599,958 B2 | 7/2003 | Lilley |
| 6,803,394 B2 | 10/2004 | Lilley et al. |
| 8,263,677 B2 | 9/2012 | Conger et al. |
| 8,367,405 B2 | 2/2013 | Gronthos et al. |
| 8,367,742 B2 | 2/2013 | Vu et al. |
| 8,399,537 B2 | 3/2013 | Conger et al. |
| 8,492,454 B2 | 7/2013 | Vu et al. |
| 8,541,482 B2 | 9/2013 | Vu et al. |
| 8,697,619 B2 | 4/2014 | Steffier et al. |
| 2007/0066704 A1 | 3/2007 | Schwalm et al. |
| 2010/0168320 A1 | 7/2010 | Schwalm et al. |
| 2012/0004340 A1 | 1/2012 | Raney et al. |
| 2012/0040120 A1 | 2/2012 | Schwalm et al. |

FOREIGN PATENT DOCUMENTS

| | | |
|---|---|---|
| WO | WO2011011304 A2 | 1/2011 |
| WO | WO2013139565 A1 | 9/2013 |
| WO | WO2013154845 A1 | 10/2013 |
| WO | WO2013192515 A1 | 12/2013 |

*Primary Examiner* — James W Rogers
(74) *Attorney, Agent, or Firm* — Christopher R. Lewis

(57) ABSTRACT

Disclosed herein are coating compositions that may include at least one urethane (meth)acrylate oligomer having a molecular weight between about 2,000 g/mol and about 50,000 g/mol and at least one cycloaliphatic (meth)acrylate. The coating compositions may also optionally include at least one photo-initiator, adhesion promoter, pigment, dye and/or plasticizer. The coating compositions may be hardened, after application, by curing by exposure to radiant energy, by exposure to electron beam radiation, by exposure to heat, by exposure to chemicals and combinations thereof. Upon hardening, the coating composition typically has two phases, a soft phase which has a Tg between −50° C. and 0° C. and a hard phase which has a Tg between 60° C. and 120° C. Methods of using the coating compositions are also described.

22 Claims, No Drawings

REMOVABLE COATING SYSTEMS AND METHODS

CROSS-REFERENCE TO RELATED APPLICATIONS

This application is a U.S. national stage application under 35 U.S.C. § 371 of PCT/EP2015/075970, filed Nov. 6, 2015, which claims benefit to U.S. patent application No. 62/076,706, filed Nov. 7, 2014.

FIELD OF THE INVENTION

Disclosed herein are coating compositions for nail cosmetics. More particularly, disclosed herein are coating compositions that may include at least one urethane (meth)acrylate oligomer and at least one cycloaliphatic (meth)acrylate. The coating compositions may also optionally include at least one photo-initiator, adhesion promoter, pigment, dye and/or plasticizer. Certain embodiments of the coating compositions disclosed herein are advantageous with respect to durability, adhesion, removability, scratch resistance, impact resistance and aesthetics such as shine.

BACKGROUND OF THE INVENTION

Consumers use nail coatings to cosmetically enhance the appearance of nails and/or to protect them. Currently, there is market demand from consumers for increasingly durable nail cosmetic compositions that are more convenient to apply to the nail and more convenient to remove therefrom.

Conventional nail coatings can be classified into two main categories: nail polishes and gel systems. Nail polishes typically comprise various solid components which are dissolved and/or suspended in non-reactive solvents. Upon application and drying, the solid components deposit on the nail surface as a hardened layer that is clear, translucent or colored. Nail polishes, however, are easily scratched and may chip or peel from the nail in a short period of time, such as from one to five days. Gel systems comprise a gel that may be brushed onto nails and subsequently cured. Because gel systems are usually cross-linked thermoset systems, they are highly durable with excellent scratch and solvent resistance. However, thermosets are harder to remove from nails (compared to nail polishes) and may require soaking the nail in non-reactive organic solvents for about 30 to about 90 minutes and may also require mechanical assistance for complete removal. Also, gel systems may undergo shrinkage or pull-back during curing, which is a reduction in the area coated, most frequently observed near or at the edges of the nail. This arises from the surface tension and/or irregular shape of nails and may cause the gel to agglomerate and/or run.

U.S. Pat. Nos. 8,263,677 and 8,399,537 disclose the use of at least one non-reactive, solvent-dissolvable polymer in a nail cosmetic composition to create voids in acrylic thermoset systems after exposure to actinic radiation. In U.S. Pat. No. 8,263,677, the compositions therein include not only reactive urethane (meth)acrylates and reactive (meth)acrylates, but also include non-reactive solvent-dissolvable polymer and non-reactive solvent. In U.S. Pat. No. 8,399,537, the compositions therein include polymer copolymerized from methyl (meth)acrylate (MMA) and methacrylic acid (PMMA) as non-reactive solvent-dissolvable polymers. They also include non-reactive solvent.

PCT/US2010/042395 discloses formulations including di-[hydroxyethyl methacrylic] trimethylhexyl dicarbamate, hydroxyethyl methacrylate, hydroxypropyl methacrylate and photoinitiator. The formulations can deliver the balance of durability and ease of removal properties, but include non-reactive solvent-dissolvable polymer and non-reactive solvent.

U.S. Pat. No. 8,367,742 discloses polymerizable compositions and color layers polymerized therefrom. These compositions include non-reactive, solvent-dissolvable polymer that aid in making the layers more solvent soakable.

U.S. Pat. No. 8,492,454 discloses polymerizable nail coatings for removable color layer. The formulations therein include one plasticizer having the general structure of RCO—OR' as well as non-reactive solvent-dissolvable polymers and non-reactive solvents.

U.S. Pat. No. 8,541,482 discloses multilayer nail covering systems comprising at least a first layer and a second layer, with one of the layers comprising HPMA. The systems also include urethane (meth)acrylates and non-reactive, solvent-dissolvable polymer and non-reactive solvents.

International Application No. PCT/US2013/034584 discloses curable coating compositions that form one layer covering systems and do not require under-coatings or over-coatings. The compositions include non-reactive, solvent-dissolvable polymers.

SUMMARY OF THE INVENTION

Known nail coating compositions suffer from a number of drawbacks, including a need for under-coatings and/or over-coatings (e.g., multilayers) to impart better adhesion, better durability and better aesthetics to the nail coating composition. Such multilayer systems may be difficult to remove from the nail once applied thereon and hardened, which may take from about 30 minutes to about 90 minutes of soaking the nail composition in organic solvent to remove. Also, known coating compositions may include non-reactive solvent-dissolvable polymer and non-reactive solvent. The non-reactive solvent is selected from ketones, alkyl acetates, alcohols, alkanes, alkenes and mixtures thereof, which gives strong odor and releases volatile organic compounds (VOC). Non-reactive solvent can evaporate when the bottle cap is removed. This can leads to the change of the recipe, subsequent solidification in the bottle. Thus, there is need to develop gel nail products without non-reactive solvent and develop a single layer system which can offer all the properties balance (adhesion and gloss, removability and durability) instead of multilayers to deliver different perspective of the properties. Such a system would have environmental and economic values.

Embodiments of the disclosed embodiment overcome at least some of the drawbacks associated with known nail coating compositions. Once applied on a nail (such as a fingernail and/or a toenail) and hardened, certain embodiments of the coating compositions described herein may be easily removed from the nail by exposing the coating composition to an organic solvent, for example, by soaking the coated nail in organic solvent for less than 5 minutes. Further, certain embodiments of the coating compositions described herein may have increased durability (e.g., hardness, scratch resistance, etc.) of the coating compositions when hardened, which eliminates the need for an over-coating. And, the coating compositions described herein may have increased adhesion to the nail, which may eliminate the need for an under-coating. Thus, the coating compositions described herein may lead to elimination of the need for multilayer coatings (e.g., of three layers coatings) because one layer leads to the desired performance and aesthetics. The coating compositions described herein also avoid the use of non-reactive solvent. The coating compositions described herein are suitable for use in nail cosmetics and for nail coatings.

In embodiments, a coating composition is described which comprises: a) at least one urethane (meth)acrylate oligomer; b) at least one cycloaliphatic (meth)acrylate; and c) optionally, at least one allylic compound from allylic monomers and/or oligomers bearing at least one allylic group; and d) optionally at least one component selected from the group consisting of an adhesion promoter, a photo-initiator, a pigment, a dye, a plasticizer and combinations thereof.

In embodiments, the at least one urethane (meth)acrylate oligomer a) may be described according to formula (I) below:

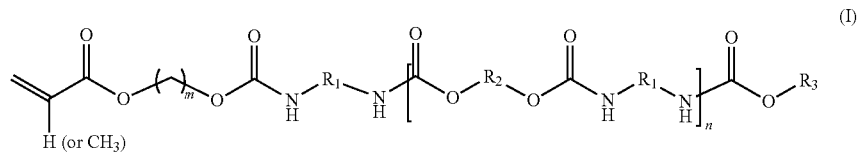

(I)

wherein 2≤n≤20 and 2≤m≤4; $R_1$ being a diisocyanate radical selected from the group consisting of alkylene, cycloalkylene, arylene, arylkylene and combinations thereof; $R_2$ being a diol radical selected from the group consisting of alkylenes, cycloalkylenes, arylalkylenes and combinations thereof; $R_3$ comprises a moiety of —$R_4$—OH that has a mean free OH value of about 0.01 mg KOH/g to about 100 mg KOH/g and $R_3$ comprises a moiety of —$R_5$-(meth)acryloyl; $R_4$ and $R_5$ being a bivalent radical selected from the group consisting of alkylenes, cycloalkylenes, arylalkylenes and combinations thereof; and wherein at least one urethane (meth)acrylate oligomer has a molecular weight of from about 2,000 g/mol to about 50,000 g/mol, preferably from 3,000 g/mol to 25,000 g/mol. Said molecular weight generally (for the specification) corresponds to the number average molecular weight Mn as measured by GPC in THF with polystyrene standards.

In embodiments, the at least one urethane (meth)acrylate oligomer may be derived from polyethers, polyesters, polycarbonates and/or polycaprolactones and have an average in number-functionality of from about 1.1 to about 1.9. In embodiments, the at least one urethane (meth)acrylate oligomer may have a molecular weight Mn of from about 3,000 g/mol to about 25,000 g/mol and a mean OH value from about 2 mg KOH/g to about 50 mg KOH/g. A suitable method for determining OH value is as defined in the experimental part for examples.

In embodiments, the cycloaliphatic (meth)acrylate b) comprises a (meth)acrylate monomer bearing at least one mono-, bi- or tri-cyclic group and may be selected from the group consisting of (meth)acrylates of dicyclopentadienyl, cyclopentadienyl, isobornyl, cyclohexyl, isophoryl, tetrahydrophthaloyl, tricyclodecanoyl, hydrogenated naphthoyl, norbornyl, derivatives of abietic acid and combinations thereof. The cycloaliphatic (meth)acrylate preferably is be selected from the group consisting of 3,3,5-Trimethycyclohexyl acrylate, tricyclodecane dimethanol (meth)acrylate (including diacrylate), (alkoxylated) isobornyl (meth)acrylate, (alkoxylated) isophoryl (meth)acrylate, (alkoxylated) trimethylolpropane cyclic formal (meth)acrylate, (alkoxylated) tertiobutylcyclohexyl (meth)acrylate, (alkoxylated) tetrahydrofurfuryl (meth)acrylate, (alkoxylated) dicyclopentadiene (alkoxylated) (meth)acrylate, (alkoxylated) tricyclodecane dimethanol (meth)acrylate, (alkoxylated) cyclohexane dimethanol (meth)acrylate, (alkoxylated) (di) cyclopentenyl (meth)acrylate, (alkoxylated) cyclohexyl (meth)acrylate, (alkoxylated) norbornyl (meth)acrylate, (alkoxylated) (meth)acrylate based on rosin (hydroxyalkyl (meth)acrylate ester with abietic acid) and combinations thereof.

In embodiments, the cycloaliphatic (meth)acrylate is present from 20 to 80%, preferably from 35 to about 70% by weight in the coating compositions.

In embodiments, the coating compositions include at least one photo-initiator and are UV and LED curable, wherein the photo-initiator may be selected from the group consisting of α-hydroxyketones, phenylglyoxylates, benzyldimethylketals, α-aminoketones, mono-acyl phosphines, bis-acyl phosphines, phosphine oxides, metallocenes and combinations thereof. Tertiary amine coinitiators may be added to enhance the cure speed.

In embodiments, the coating compositions may or may not include adhesion promoter that includes one or more functional groups selected from the group consisting of hydroxyl groups, carboxylic acids, phosphoric acids and combinations thereof. In embodiments, the at least one adhesion promoter may be selected from the group consisting of hydroxylethyl (meth)acrylate, hydroxylpropyl (meth) acrylates, pyromellitic dianhydride dialkyl(meth)acrylate, phathalic acid monoalkyl (meth)acrylates, succinic acid monoalkyl (meth)acrylates, phosphoric acid or phosphoric ester functional (meth)acrylates and carboxylic acid functional (meth)acrylates and combinations thereof.

In embodiments, the coating compositions do not comprise substantial amounts, if any, of non-reactive solvent and/or do not comprise any non-reactive and solvent-dissolvable polymer. In embodiments, the coating compositions after cure have two phases, a soft phase with a glass transition temperature Tg of between −50 and 0° C. and a hard phase with a Tg of between 60° C. and 120° C. The Tg is measured by DMA (Dymamic mechanical analysis) method at a heating rate of 3° C./min at the tan delta peak, as defined in the experimental part for examples.

In embodiments, a method of using the coating compositions described herein may comprise applying the coating compositions to a nail and hardening the coating composition. In embodiments, hardening the compositions may comprise curing the coating compositions by exposure to radiant energy (such as visible light, light-emitting diode (LED) light and/or UV light) or by exposure to electron beam radiation or by exposure to heat or by chemical curing. The curing may also comprise dual curing using combinations of curing techniques.

Embodiments of the coating compositions described herein are adapted to form smooth, uniform layers that substantially conform to the surface of a nail. Embodiments of the coating compositions disclosed herein are advantageous with respect to durability, adhesion, removability, scratch resistance, impact resistance and/or aesthetics such as shine.

DETAILED DESCRIPTION OF THE INVENTION

The coating compositions described herein comprises a) at least one urethane (meth)acrylate oligomer and b) at least one cycloaliphatic (meth)acrylate. The compositions may also optionally comprise allylic compound and other additives, such as at least one photo-initiator, adhesion promoter, pigment, dye and/or plasticizer.

Particularly, the coating composition according to the present invention comprises:
a) at least one urethane (meth)acrylate oligomer of formula (I)

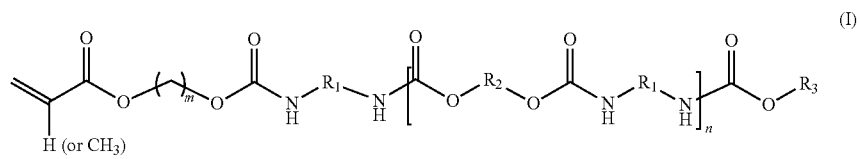

wherein $2 \leq n \leq 20$ and $2 \leq m \leq 4$;
$R_1$ being a diisocyanate radical selected from the group consisting of alkylene, cycloalkylene, arylene, arylkylene and combinations thereof;
$R_2$ being a diol radical selected from the group consisting of alkylenes, cycloalkylenes and arylalkylenes and combinations thereof;
$R_3$ comprises a moiety of $-R_4-OH$ that has a mean free OH value of about 0.01 mg KOH/g to about 100 mg KOH/g and $R_3$ comprises a moiety of $-R_5$-(meth)acryloyl;
$R_4$ and $R_5$ being a bivalent radical selected from the group consisting of alkylenes, cycloalkylenes and arylalkylenes, with $R_4$ and $R_5$ being identical or different from each other; and
wherein the at least one urethane (meth)acrylate oligomer has a number average molecular weight Mn measured by GPC of from about 2,000 g/mol to about 50,000 g/mol;
b) at least one cycloaliphatic (meth)acrylate; and
c) optionally, at least one allylic compound from allylic monomers and/or oligomers bearing at least one allylic group,
d) optionally, at least one component selected from the group of additives consisting of an adhesion promoter, a thiol compound, a photo-initiator, a pigment, a dye, a plasticizer and combinations thereof.

Preferably, said coating composition is a curable coating composition.

The coating composition of the invention preferably gives a coating after curing which has two phases, a soft phase which has a Tg between −50° C. and 0° C. and a hard phase which has a Tg between 60° C. and 120° C., with Tg being measured by DMA at tan delta peak (temperature). According to a particular embodiment, said coating composition comprises less than 1% by weight of non-reactive solvent and less than 1% by weight of non-reactive, solvent-dissolvable polymer.

I—Urethane (Meth)Acrylate Oligomer

In embodiments, the at least one urethane (meth)acrylate oligomer may be described by the structure of formula (I) below with same meaning of $R_1$, $R_2$, $R_3$ and m and n, as defined above.

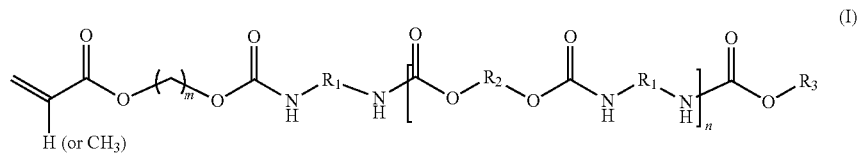

The at least one urethane (meth)acrylate oligomer may be derived from polyethers, polyesters, (hydrogenated)polybutadiene, polycarbonates and/or polycaprolactones.

Preferably, n (e.g., the number of urethane repeating units) may have a value from 2 to 20 or from 3 to 10 or from 3 to 5. Preferably, m (e.g., the number of methylene repeating units) may have a value from 2 to 4. The at least one urethane (meth)acrylate oligomer may have a backbone comprising free OH groups. The mean free OH value of the oligomer, including di-functional, mono-functional and non-functional oligomer, may be from about 0.01 mg KOH/g to about 100 mg KOH/g or from about 0.5 mg KOH/g to about 100 mg KOH/g or from about 1 mg KOH/g to about 50 mg KOH/g or from about 2 mg KOH/g to about 50 mg KOH/g or from about 3 mg KOH/g to about 10 mg KOH/g. The at least one urethane (meth)acrylate oligomer has an average in number-acrylate or methacrylate functionality of from about 1 to about 2 which is less than 2 or from about 1.1 to about 1.9 or from about 1.2 to about 1.8 or from about 1.3 to about 1.7 or less than 2.

In embodiments, $R_1$ may be a diisocyanate radical selected from the group consisting of alkylene, cycloalkylene, arylene, arylkylene and combinations thereof; $R_2$ may be a diol radical selected from the group consisting of alkylenes, cycloalkylenes, arylalkylenes and combinations thereof; $R_3$ comprises a moiety of —$R_4$—OH so that it (oligomer a)) has a free OH value of about 0.01 mg KOH/g to about 100 mg KOH/g and $R_3$ comprises a moiety of —$R_5$-(meth)acryloyl; $R_4$ and $R_5$ being a bivalent radical selected from the group consisting of alkylenes, cycloalkylenes, arylalkylenes and combinations thereof, with $R_4$ and $R_5$ being identical or different from each other.

In embodiments, the at least one urethane (meth)acrylate oligomer may have a molecular weight Mn (as measured by GPC as defined above) of from about 1,000 g/mol to about 200,000 g/mol or from about 2,000 g/mol to about 50,000 g/mol and preferably from about 3,000 to 25,000 and more preferably from 5,000 g/mol to about 25,000 g/mol. In embodiments, the at least one urethane (meth)acrylate oligomer may be present in the coating composition at from about 5 to about 80% by weight, preferably from 10 to 80%, more preferably from 20 to 80% or from about 20 to about 60% by weight or from about 35 to about 50% by weight. Weight % of a)+b)+c)+d) sums to 100%.

II—Cycloaliphatic (Meth)Acrylate

In embodiments, the at least one cycloaliphatic (meth)acrylate may comprise a (meth)acrylate monomer bearing at least one mono-, bi- or tri-cyclic group. The cycloaliphatic moiety may be selected from the group consisting of (meth)acrylates of dicyclopentadienyl, cyclopentadienyl, isobornyl, cyclohexyl, isophoryl, tetrahydrophthaloyl, tricyclodecanoyl, hydrogenated naphthoyl, norbornyl, derivatives of abietic acid and combinations thereof. The cycloaliphatic (meth)acrylate preferably is be selected from the group consisting of 3,3,5-Trimethycyclohexyl acrylate, tricyclodecane dimethanol (meth)acrylate (including diacrylate), (alkoxylated) isobornyl (meth)acrylate, (alkoxylated) isophoryl (meth)acrylate, (alkoxylated) trimethylolpropane cyclic formal (meth)acrylate, (alkoxylated) tertiobutylcyclohexyl (meth)acrylate, (alkoxylated) tetrahydrofurfuryl (meth)acrylate, (alkoxylated) dicyclopentadiene (alkoxylated) (meth)acrylate, (alkoxylated) tricyclodecane dimethanol (meth)acrylate, (alkoxylated) cyclohexane dimethanol (meth)acrylate, (alkoxylated) (di)cyclopentenyl (meth)acrylate, (alkoxylated) cyclohexyl (meth)acrylate, (alkoxylated) norbornyl (meth)acrylate, (alkoxylated) (meth)acrylate based on rosin (hydroxyalkyl (meth)acrylate ester with abietic acid and combinations thereof.

In embodiments, more preferably the at least one cycloaliphatic (meth)acrylate may be chosen from the group consisting of isobornyl acrylate, tricyclodecane dimethanol diacrylate, 3,3,5-trimethylcyclohexyl acrylate and combinations thereof. The coating compositions may comprise at least two different cycloaliphatic (meth)acrylates.

In embodiments, the at least one cycloaliphatic (meth)acrylate b) may be present in the coating composition at from about 20 to 95%, preferably from 20 to about 80% by weight or from about 30 to about 75% by weight or from about 40 to about 65% by weight or from about 50 to about 60% by weight.

III—Allylic Compounds c)

The coating composition of the present invention may further comprise and preferably further comprises in addition to components a) and b) as defined above, an additional component c) which is at least one allylic compound chosen from monomers and/or oligomers (oligomers also called resins), bearing at least one allylic group. The allylic group can be represented by formula: $CH_2$=$CHCH_2$—. Such an allylic compound according to component c) can overcome oxygen inhibition and improve the surface cure of the coating. Suitable allylic compounds c) may be selected from monofunctional and/or multifunctional allylic monomers and/or oligomers, preferably from multifunctional monomers and/or oligomers bearing at least two allylic groups $CH_2$=$CHCH_2$—.

Suitable allylic compounds c), either monomers or oligomers may be terminated with allylic ether groups according to $CH_2$=$CHCH_2$—O— or with allylic esters according to $CH_2$=$CHCH_2$—OC(=O)—. As suitable examples of allylic compounds c) can be cited: trimethylol propane diallyl either, the reaction product of trimethylol diallyl ether (monoalcohol) with a diisocyanate such as isophorone diisocyanate or 4,4"-Methylenedicyclohexyl diisocyanate or hexamethylene diisocyanate leading to a diurethane derivative bearing 4 allylic ether groups, ditrimethylolpropane triallyl ether or its reaction product (diurethane) with a diisocyante as defined above leading to a diurethane derivative bearing 6 allylic ether groups.

The weight content of the said allylic compounds c), when present, may be up to 30% (between 0 and up to 30%), preferably up to 20% and more preferably up to 10% w/w of the coating composition of the invention (vs sum of a)+b)+c)+d)).

Along with said allylic compounds c), the coating composition of the present invention may further comprise and preferably comprises a metal ion catalyst including, but not limited to, Cobalt-, Maganese-, Iron-, Vanadium- or Zirconium-based solutions. As more particular examples can be cited iron sulfate, cobalt naphtehnate, 2-ethyl hexanoate cobalt. The weight content of said metal ion catalyst when present may rise up to 1000 ppm (between 0 and 1000 ppm).

More particularly, the coating composition of the invention comprises an allylic compound c) bearing at least one allylic group and optionally a metal ion catalyst.

IV—Other Additives d)

In embodiments, additives may also be included, or optionally included, in the coating compositions described herein. For example, one or more colorants (e.g., dyes, pigments), photo-initiators, thiol compounds, adhesion promoters, fillers, rheology modifiers, thixotropic agents, plasticizers, UV absorbers, UV stabilizing agents and/or dispersants may be included.

In embodiments, there may be present no adhesion promoters in the coating compositions, as the oligomers themselves possess sufficient adhesion properties. However, adhesion promoters may be added to the coating compositions to further increase the adhesion of the coating compositions directly to the nail. The coating compositions may be formulated such that they are adapted to adhere to the nail for at least 5 days, or for at least 7 days, or for at least about 14 days.

Suitable adhesion promoters for use in the coating compositions described herein may include compounds that include at least one functional group selected from the group consisting of hydroxyl groups, carboxylic acids, phosphoric acids, ethers, acetoxy groups and combinations thereof. Suitable adhesion promoters may include compounds selected from the group consisting of hydroxyalkyl (meth)acrylates, pyromellitic dianhydride di(meth)acrylate, pyromellitic di(meth)acrylate, pyromellitic dianhydride glyceryl dimethacrylate (PMGDM), methacroyloxyethyl maleate, 2-hydroxyethyl (meth)acrylate, monoalkyl maleates, phthalic acid monoalkyl (meth)acrylates, phosphoric and carboxylic functional (meth)acrylates such as hydroxyethyl (meth)acrylate phosphate, maleate or succinate, hydroxypropyl (meth)acrylate phosphate, maleate or succinate, tetrahydrofurfuryl (meth)acrylate, glycerol phosphate di(meth)acrylate, ethoxyethyl (meth)acrylate, 2-phenoxyethyl methacrylate, alkoxylated bisphenol A di(meth)acrylate, alkoxylated trimethlolpropane triacrylate, alkoxylated nonyl phenol (meth)acrylate, methoxy or propoxy polyethylene glycol mono(meth)acrylate, alkoxylated pentaerythritol tri or tetraacrylate, diethylene glycol methyl ether (meth)acrylate, triethylene glycol ethyl ether (meth)acrylate, polyether acrylate oligomer, polypropylene glycol di(meth)acrylate, polyethylene glycol di(meth)acrylate, neopentylglycol di(meth)acrylate, trimethylolpropane triglycidyl ether, lauryl glycidyl ether, n-butyl glycidyl ether, 1,4-butanediol diglycidyl ether, poly (ethylene glycol) methyl ether (meth)acrylate, 1,6-hexanediol diglycidyl ether, trimethylolpropane triacrylate, HEMA polyethoxy ethyl methacrylate, polyethylene glycol methyl ether (meth) acrylate, aceto acetoxy ethyl methacrylate, and combinations thereof. Preferably, the adhesion promoters are selected from the group consisting of hydroxyethyl (meth) acrylate, hydroxylpropyl (meth)acrylates, pyromellitic dianhydride dialkyl(meth)acrylate, phathalic acid monoalkyl (meth)acrylates, succinic acid monoalkyl (meth)acrylates, phosphoric acid or phosphoric ester functional (meth)acrylates and carboxylic acid functional (meth)acrylates and combinations thereof.

The amount of adhesion promoter in the coating compositions described herein may be adjusted to achieve a desired adhesion level when hardened. Preferably, the amount of adhesion promoter is from about 0.1% to about 30% by weight or from about 2% to about 25% by weight or from about 3% to about 20% by weight or from about 5% to about 15% by weight of the coating composition. Excessive amounts of adhesion promoter should be avoided so as not negatively affect the removability of or the aesthetics associated with, the coating compositions described herein.

Convenient thiol compounds with at least 2-SH functional groups may be for example the following ones: Pentaerythritol tetra(3-mercapto-propionate), Trimethylolpropane tri (3-mercaptopropionate), Glykoldi(3-mercaptopropionate), Pentaerythritol tetramercaptoacetate, Trimethylolpropane trimercaptoacetate, Glycol dimercaptoacetate, Di-Pentaerythritol hexakis(3-mercaptopropionate) or Tris[2-(3-mercaptopropionyloxy) ethyl]isocyanurate.

A typical amount of such a thiol compound in the coating composition of the present invention may be up to 10%.

In embodiments, sufficient amounts of at least one photo-initiator may be included in the coating composition so as to render the composition as curable. Preferably, the coating compositions may include from about 0.1% by weight to about 20% by weight of at least one photo-initiator, preferably about 5% to about 15% by weight. Suitable photo-initiators for use in the coating compositions described herein may include compounds selected from the group consisting of α-hydroxyketones, phenylglyoxylates, benzyldimethylketals, α-aminoketones, mono-acyl phosphines, bis-acyl phosphines, phosphine oxides, metallocenes and combinations thereof.

In embodiments, the at least one photo-initiator may be 1-hydroxy-cyclohexyl-phenyl-ketone, diphenyl (2,4,6-trimethylbenzoyl)-phosphine oxide, 2-hydroxy-2-methyl-1-phenyl-1-propanone, phenyl bis (2,4,6-trimehylbenzoyl) phosphoine oxide or combinations of them.

In embodiments, sufficient amounts of at least one pigment, dye or plasticizer may be included in the coating compositions described herein. Such additives promote the aesthetic appearance of the nail after coating and hardening. Such additives may be present in the coating compositions described herein from about 0.1% by weight to about 20% by weight or from about 1% to about 10% by weight.

The coating compositions described herein may be applied directly to the nail surface with no under-coating. It may be beneficial, however, if desired, to clean the nail surface of any residuals before applying the coating compositions. Once applied, the coating compositions may be hardened by curing. Curing techniques are not particularly limited and may include techniques that expose the compositions to polymerization accelerants. Such techniques may include exposure to radiant (radiation) energy such as visible radiation, UV radiation, LED radiation or by exposure to electron-beam radiation. Such techniques may include exposure to heat and exposure to chemicals, such as crosslinkers, thermal conduction, thermal radiation, amines, peroxides and combinations thereof. The time period of exposure is not particularly limited, so long as the time period is effective to harden (e.g., cure) the coating compositions.

In certain instances, it may be desirable to use dual-cure techniques directed to combinations of the aforementioned curing techniques. While the acrylate groups can be polymerized through the above techniques, the hydroxyl groups in the coating compositions may also react with external —OH reactants such as isocyanates, amines, anhydrides or acids. The reactions with external —OH groups may be initiated first, followed by acrylate polymerization or vice versa. Upon hardening, the coating compositions become solidified, such that no top coating is needed because the coating compositions are able to achieve desirable levels of aesthetics (such as a smooth and glossy finish) and desirable levels of durability with respect to routine exposure to mechanical impact, abrasion, water immersion, etc. However, if desired, a top coat may be applied to a nail. If also desired, multiple coatings of the coating compositions may be applied, with subsequent curing after each coating application.

In embodiments and once a layer of the coating compositions described herein have been applied to the nail, the layer may be exposed to radiant energy (e.g., UV light, visible light and/or LED light) for a time effective to cause cross-linking of the at least one urethane (meth)acrylate oligomer and at least one cycloaliphatic (meth)acrylate to harden the applied composition. The intensity and wavelength of the radiation may be adjusted as desired to achieve the desired extent of hardening. Time frames for exposure to radiant energy to cause sufficient cross-linking is not particularly limited and may be from at least about 2 minutes or at least about 5 minutes or at least about 10 minutes or at least about 15 minutes or at least about 20 minutes.

Accordingly, a method of using the coating compositions described herein may comprise applying the coating composition to a nail, followed by hardening (curing) of the composition on the nail by curing or by drying. Optionally, cleaning the nail prior to application of the coating compositions thereon may be performed.

Once hardened, certain embodiments of the coating compositions described herein may be easily removed from the nail by exposing the coating composition to an organic solvent such as acetone. Other solvents for removal may be butyl acetate, isopropyl alcohol, ethanol, ethyl acetate, methyl acetate, methyl ethyl ketone and mixtures thereof. Such exposure may be in the form of soaking the coated nail in the organic solvent. Preferably, the cured coating composition are adapted to be removed from the nail by soaking the coated nail in organic solvent for less than 10 minutes or less than 5 minutes or less than 3 minutes or less than 1 minute. Preferably, the coating compositions described herein are adapted to be removed from the nail by only soaking in an organic solvent and without a need for any other type of removal treatment, such as mechanical treatment.

Without wishing to be bound by any theory, it is believed that the coating compositions disclosed herein are able to avoid the drawbacks associated with known coating compositions due to a number of factors which may be present individually or in any combination in coating compositions according to this disclosure, including:

high molecular weight urethane meth(acrylate) oligomers in the range of about 2,000 g/mol 50,000 g/mol; b) lower average in number-functionality of the urethane meth(acrylate) oligomers in the range of from about 1.1, preferably 1.2 to about 2 meaning less than 2;

mean hydroxyl value in the urethane meth(acrylate) oligomers is in the range of from about 0.01 mg KOH/g to about 100 mg KOH/g;

the coating compositions comprising minimal, if any, non-reactive solvent and comprising minimal, if any, non-reactive and solvent-dissolvable polymer; and after curing, the coatings have two glass transition temperatures (Tg), one Tg is between −50° C. and 0° C., the other Tg is between 60° C. and 120° C. Tg is measured by DMA at a heating rate of 3° C./min, at tan delta peak. Such properties of the coating compositions described herein help lead to increased durability (e.g., hardness, scratch resistance, etc.) of the coating compositions when hardened, which eliminates the need for an over-coating. Such properties also include increased adhesion to the nail, which eliminates the need for an under-coating. Thus, the coating compositions described herein may lead to elimination of the need for multilayer coatings (e.g., of three layers coatings) because one layer leads to the desired performance and aesthetics.

It is believed that, with respect to removability of the hardened coating compositions described herein, the low density of cross-linking (due to low functionality) upon curing between the at least one urethane (meth)acrylate oligomer and at least one cycloaliphatic (meth)acrylate allows for organic solvent to penetrate more easily and more deeply into the hardened coating composition, leading to the significantly shortened time periods for complete removal of the coating composition. Herein, cross-link density can be described as the number of chain segments (between cross-links) per unit volume. It is also believed that, the cured coatings have two phases, the soft phase with Tg between −50° C. and 0° C. offers good adhesion on nails and the hard phase with Tg between 60° C. and 120° C. offers durability, preserves the hardness, stain resistance and scratch resistance of the cured coating compositions while avoiding tackiness of the same. Tg is measured by DMA as already disclosed above.

In embodiments, the coating composition comprises less than 5% by weight of non-reactive solvent and/or non-reactive, solvent-dissolvable polymer or less than 3% by weight of non-reactive solvent and/or non-reactive, solvent-dissolvable polymer or less than 1% by weight of non-reactive solvent and/or non-reactive, solvent-dissolvable polymer or less than 0.5% by weight of non-reactive solvent and/or non-reactive, solvent-dissolvable polymer. Preferably, the coating compositions do not comprise any non-reactive solvent and does not comprise any non-reactive and solvent-dissolvable polymer. The non-reactive, solvent-dissolvable polymers may be film formers such as cellulose ester including cellulose acetate, cellulose acetate butyrate and ethyl cellulose, polyesters, polyurethanes, alkyd resins and polyvinyl resins such as polyvinyl acetate, polyvinyl chloride, polyvinylbutyrate, (meth)acrylic and vinyl copolymers such as styrene/butadiene copolymers, acrylate/vinyl acetate copolymers, acrylonitrile/butadiene copolymers, ethylene/vinyl acetate copolymers, methacrylate-polymethacrylic acid (PMMA-PMAA) copolymer. The non-reactive solvents may be ketones such as acetone or methyl ethyl ketone, alkyl acetates such as ethyl acetate or butyl acetate, alcohols such as isopropyl alcohol and ethanol; alkanes such as hexane, alkenes such as toluene and mixtures thereof. The amounts in w/w % of all of the components of the said coating composition are chosen so that the sum of all the components of the composition including a)+b) and optional c) or d) and other possible components as defined above, is 100%.

EXAMPLES

Example 1

Oligomer 1

The components and respective amounts used in oligomer 1 are shown in Table 1.

TABLE 1

| Component | Amount |
| --- | --- |
| 3-isocyanatomethyl-3,5,5-trimethylcyclohexyl isocyanate | 55.58 grams |
| Triphenylphosphite | 0.38 grams |
| 2,6-Bis(1,1-dimethylethyl)-4-methylphenol | 0.38 grams |
| Bismuth Octoate | 0.19 grams |
| 2-hydroxyethyl acrylate | 11.61 grams |
| Isobornyl Acrylate | 61.0 grams |
| Ethylene glycol-butylene glycol-adipate diol | 277.27 grams |

The OH/NCO molar ratio in this example was 1.05. First, 55.58 grams of 3-isocyanatomethyl-3,5,5-trimethylcyclohexyl isocyanate, 0.38 grams of Triphenylphosphite (inhibitor), 0.38 grams of 2,6-Bis(1,1-dimethylethyl)-4-methylphenol (BHT; inhibitor), 61.0 grams of Isobornyl Acrylate, 11.61 grams of 2-hydroxyethyl acrylate and 277.27 grams of Ethylene glycol-butylene glycol-adipate diol under commercial name Piothane® 46-1300 EBA (Mn of 1300 and with molar ratio of EG/BG: 4/6) supplied by Panolam Surface Systems, were charged into a 1 L reaction flask equipped with an agitator, liquid addition funnel, thermometer and gas inlet tube. This mixture was heated to 40° C. under agitation and dry air sparge. Next, 0.19 grams of Bismuth Octoate (catalyst) were charged. After the exotherm, the reactor was heated to 85° C. The reaction was held at 85° C. for at least 3 hours, until the level of NCO % was equal to or lower than 0.06%. The heater and agitation were turned off. Once the reactor temperature cooled to 60° C., the product was poured out into a container and testing on the final properties was performed. The oligomer is recovered including isobornyl acrylate as diluent. Isobornyl acrylate in the recovered oligomer is about 15 wt %.

Properties of the Oligomer 1 of Example 1

The resulting product was a clear liquid having a viscosity of 23,700 cP (mPa·s) at 60° C. (as measured by a Brookfield viscometer).

The molecular weight and polydispersity of Example 1 were determined by conventional gel permeation chromatography (GPC). A small sample was dissolved in tetrahydrofuran (THF) and injected into a liquid chromatograph (Agilent 1100 Series) equipped with HP PLGel® GPC columns (5 μm, 100 A, 250×4.6 mm; 3 μm MiniMix-E, 250×4.6 mm and 5 μm MiniMix-D, 250×4.6 mm). The components of the sample were separated by the GPC columns based on their molecular sizes in solution. The components were detected by a Hewlett-Packard 1047A® refractive index detector and recorded by Agilent HPLC Chemstation® and Polymer Laboratories GPC software. Polystyrene standards of known molecular weight and narrow dispersity were used to generate a calibration curve. The results of these tests are given in Table 2 below.

TABLE 2

Characteristics of oligomer 1 (without any diluent)

| Product | Theoretical Functionality | Experimental OH value (mg KOH/g) | Mn (GPC) | Mw (GPC) | Repeating units, n | Equivalent Mn Per Acrylate |
| --- | --- | --- | --- | --- | --- | --- |
| Oligomer 1 | 1.6 | 8.76 | 7,092 | 16,669 | 4 | 4433 |

The OH value of the oligomer 1 of Example 1 (with 15% isobornyl acrylate diluent) was determined by Radiometer TitreLab® TM865 Autotitrator. A 4-5 gram sample was dissolved in 25 ml tetrahydrofuran (THF), then 25 ml p-toluenesulfonyl isocyanate (TSI) reagent was added volumetrically and stirred for 10 minutes. The sample was then titrated with 0.25 M concentration tetrabutylammonium hydroxide. The results were reported in mg KOH/g by the autotitrator. Oligomer 1 (with diluent) was found to have an OH value of 7.45 mg KOH/g. Thus the OH value of oligomer 1 without diluent has an OH value of 8.76 mg KOH/g.

TABLE 3

Tested curable coating composition of Example 1

| | |
| --- | --- |
| Oligomer 1 (including 15% isobornyl acrylate as diluent b) | 50 wt % |
| Tricyclodecane dimethanol diacrylate (diluent b) | 25 wt % |
| 3,3,5-Trimethycyclohexyl acrylate | 20 wt % |
| 1-Hydroxy-cyclohexyl-phenyl-ketone, Photoinitiator | 5 wt % |

Example 2

TABLE 4

Tested curable coating composition of example 2

| | |
| --- | --- |
| Oligomer 1 (including 15% isobornyl acrylate as diluent b) | 47.3 wt % |
| Reaction product of trimethylol propane diallyl ether and isophorone diisocyanate (allylic compound) | 5.0 wt % |
| Tricyclodecane dimethanol diacrylate | 23.7 wt % |
| 3,3,5-Trimethycyclohexyl acrylate | 18.9 wt % |
| 6% Cobalt solution | 0.1% |
| 1-Hydroxy-cyclohexyl-phenyl-ketone, Photoinitiator | 5 wt % |

Example 3

A new oligomer, Oligomer 2, is used for the coating composition of example 3.

The components and respective amounts used for oligomer 2 in Example 3 are shown in Table 5 below.

TABLE 5

| Component | Amount |
| --- | --- |
| 3-isocyanatomethyl-3,5,5-trimethylcyclohexyl isocyanate | 51.13 grams |
| Triphenylphosphite | 0.48 grams |
| 2,6-Bis(1,1-dimethylethyl)-4-methylphenol | 0.48 grams |
| Bismuth Octoate | 0.24 grams |
| 2-hydroxyethyl acrylate | 13.35 grams |
| Isobornyl Acrylate | 79.5 grams |
| ε-Caprolactone-lactide copolymer neopentyl glycol ester diol | 368.00 grams |

The OH/NCO molar ratio in this example was 1.05. First, 51.13 grams of 3-isocyanatomethyl-3,5,5-trimethylcyclohexyl isocyanate, 0.48 grams of Triphenylphosphite (inhibitor), 0.48 grams of 2,6-Bis(1,1-dimethylethyl)-4-methylphenol (BHT; inhibitor), 79.5 grams of Isobornyl Acrylate, 13.35 grams of 2-hydroxyethyl acrylate and 368.00 grams of ε-Caprolactone-lactide copolymer neopentyl glycol ester diol (molar ratio 75/25 and Mn: 2000) under commercial name CAPA 8025D supplied by PERSTORP Company were charged into a 1 L reaction flask equipped with an agitator, liquid addition funnel, thermometer and gas inlet tube. This mixture was heated to 40° C. under agitation and dry air sparge. Next, 0.24 grams of Bismuth Octoate (catalyst) were charged. After the exotherm, the reactor was heated to 85° C. The reaction was held at 85° C. for at least 3 hours, until the level of NCO % was equal to or lower than 0.06%. The heater and agitation were turned off. Once the reactor temperature cooled to 60° C., the product was poured out into a container and testing on the final properties was performed. The oligomer is recovered including isobornyl acrylate as diluent (b). Isobornyl acrylate in the recovered oligomer 2 is about 15.5 wt %.

Properties of the Oligomer 2 of Example 3

The resulting product (oligomer 2 including isobornyl acrylate) was a clear liquid having a viscosity of 35,540 cP (mPa·s) at 60° C. as measured by a Brookfield viscometer.

The molecular weight and polydispersity of oligomer 2 of Example 3 were determined by conventional gel permeation chromatography (GPC) as disclosed above for example 1. The results of these tests are given in Table 6 below.

TABLE 6

Characteristics of oligomer 2 (without diluent) of Example 3

| Product | Theoretical Functionality | Experimental OH value (mg KOH/g) | GPC Mn | GPC Mw | Repeating Units, n | Equivalent Mn per Acrylate |
|---|---|---|---|---|---|---|
| Oligomer 2 | 1.67 | 6.4 | 10,052 | 20,542 | 3 | 6019 |

The OH value of the Example was determined by Radiometer TitreLab® TM865 Autotitrator. Oligomer 2 (including 15.5% Isobornyl acrylate diluent) was found to have an OH value of 5.4 mg KOH/g. Thus, oligomer 2 without diluent has an OH value of 6.4 mg KOH/g.

TABLE 7

Tested curable coating composition with oligomer 2 of Example 3

| | |
|---|---|
| Oligomer 2 (including 15.5% isobornyl acrylate as diluent b) | 50 wt % |
| Tricyclodecane dimethanol diacrylate | 25 wt % |
| 3,3,5-Trimethycyclohexyl acrylate | 20 wt % |
| 1-Hydroxy-cyclohexyl-phenyl-ketone, Photoinitiator | 5 wt % |

Curing Conditions, Test Methods for Cured Coating Compositions and Performances

The coating compositions were prepared, applied and cured on a belt conveyor UV curing system at a speed of 20 feet per minute. The curing energy is approximately 1 mJ/cm$^2$. The exposure to UV light is about 3 seconds.

Testing methods for determining the properties of the Examples and Comparative Examples are based on standard coating testing methods. Pencil hardnesses are determined by following the ASTM D3363-05 protocol entitled "Standard Test Methods for Film Hardness by Pencil Test". Gloss levels are determined following the ASTM D523-08 protocol entitled "Standard Test Method for Specular Gloss". Glosses are measured using a micro-TRI-gloss-meter from BYK. The initial gloss of the cured coatings indicates the shin and sheen of the nail coatings. The higher gloss unit indicates the better shinning appearance. Flexibilities are determined with a Conical Mandrel Tester by following the ASTM D522 protocol entitled "Standard Test Methods for Mandrel Bend Test of Attached Organic Coating." The distance from the farthest end of the crack to the closest end indicates the flexibility. The shorter crack distance indicates the better flexibility. If there are no cracks during the test, the distance may be marked as zero. Color is tested by BYK Gardner Color-Guide 45/0 (6807) Portable Colorimeter. The lightness, L*, represents the darkest black at L*=0 and the brightest white at L*=100. The color channels, a* and b*, will represent true neutral gray values at a*=0 and b*=0. The red/green opponent colors are represented along the a* axis, with green at negative a* values and red at positive a* values. The yellow/blue opponent colors are represented along the b* axis, with blue at negative b* values and yellow at positive b* values.

Soak off times are determined by immersion the glass slide with cured coatings in acetone and by checking the coating every five minutes and recording how much percentage of the coating is removed by acetone. Adhesion is determined by making an X-cut through the coating to the artificial nail, applying pressure-sensitive tape over the X-cut and removing the tape. The adhesion is assessed qualitatively on the 0 to 4 scale, where 0 means that four quadrants of the coating are removed while 4 means that none of the four quadrants of the coating is removed. Durability is determined by assessing by eye the coating integrity after soaking in vinegar, lemon juice, detergent or hand soap for a pre-determined period of time.

Table 8 below lists the properties for coating compositions of Examples 1-3.

TABLE 8

Properties of cured coating compositions of examples 1-3 (invention)

| | Example 1 | Example 2 | Example 3 |
|---|---|---|---|
| Pencil Hardness | F | F | F |
| Shine | | | |
| Initial Gloss values | | | |
| 20° | 109 | 111 | 110 |
| 60° | 118 | 126 | 120 |
| 85° | 94.7 | 90.2 | 97.7 |
| Flexibility (in) | | | |
| 0 = No Cracking | 0 | 0 | 0 |
| Color Change (60° C. Oven) | | | |
| Initial | | | |
| L* | 92.11 | 90.2 | 91.39 |
| a* | −1.47 | −2.48 | −1.59 |
| b* | 5.79 | 9.08 | 6.34 |
| After 2 days | | | |
| L* | 92.05 | 90.5 | 91.59 |
| a* | −1.71 | −1.85 | −1.78 |
| b* | 6.95 | 7.64 | 7.48 |
| After 4 days | | | |
| L* | 91.92 | 90.5 | 91.63 |
| a* | −1.67 | −1.73 | −1.78 |
| b* | 7.07 | 7.67 | 7.64 |
| Soak-off | | | |
| After 5 minutes in acetone | 100% Loss | 100% Loss | 100% Loss |
| Adhesion on artificial nail | 4 | 4 | 4 |
| Durability, After soaking 4 days in | | | |
| Vinegar | 0% Loss | 0% Loss | 0% Loss |
| Lemon Juice | 0% Loss | 0% Loss | 0% Loss |
| Detergent | 0% Loss | 0% Loss | 0% Loss |
| Hand soap | 0% Loss | 0% Loss | 0% Loss |

As can been seen, the Examples show low color change initially, after 2 days and after 4 days; show good removability in acetone and are completely removed from a nail in 5 minutes or less. The Examples also adhere well to artificial nails and are highly durable, as shown by no loss of coating after 4 days of soaking in vinegar, lemon juice, detergent and hand soap. The Examples are very flexible, with no cracking observed. The Examples demonstrate good scratch resistance. The Examples show "F" scale of pencil hardness and the Examples are all high gloss.

COMPARATIVE EXAMPLES

Example 4 is a comparative example. A new oligomer, Oligomer 3, is used for the coating composition of said example 4 as a comparative example.

The components and respective amounts used for oligomer 3 in Example 4 as comparative example are shown in Table 9 below.

TABLE 9

Components and proportions for Oligomer 3

| Component | Amount |
| --- | --- |
| 3-isocyanatomethyl-3,5,5-trimethylcyclohexyl isocyanate | 100.2 grams |
| Thiodiethylene bis[3-[3,5-di-tert-butyl-4-hydroxyphenyl]-propionate] | 0.46 grams |
| 2-hydroxyethyl acrylate | 54.6 grams |
| Bismuth Octoate | 0.15 grams |
| Ethylene glycol adipate diol | 144.6 grams |

First, 100.2 grams of 3-isocyanatomethyl-3,5,5-trimethylcyclohexyl isocyanate, 0.46 grams of Thiodiethylene bis[3-[3,5-di-tert-butyl-4-hydroxyphenyl]propionate] (inhibitor), 54.6 grams of 2-hydroxyethyl acrylate and 144.6 grams of ethylene glycol adipate diol (Mn: 650) were charged into a 1 L reaction flask equipped with an agitator, liquid addition funnel, thermometer and gas inlet tube. This mixture was heated to 40° C. under agitation and dry air sparge. Next, 0.15 grams of Bismuth Octoate (catalyst) were charged. After the exotherm, the reactor was heated to 85° C. The reaction was held at 85° C. for at least 3 hours, until the level of NCO % was equal to or lower than 0.06%. The heater and agitation were turned off. Once the reactor temperature cooled to 60° C., the product was poured out into a container and testing on the final properties was performed. There is no monomer diluent in oligomer 3.

Table 10 below provides structural characteristics for the oligomer 3 (e.g., urethane acrylate oligomer) of Example 4 (comparative). The oligomer is a di-functional urethane acrylate without free OH groups in the backbone. Coating composition of Example 4 as comparative example includes similar amounts (e.g., wt %) of oligomers, cycloaliphatic methacrylates and photo-initiators as in Examples 1-3. However, certain characteristics of Comparative Example 4 are different than those of Examples 1-3.

TABLE 10

Structural Characteristics of Oligomer 3 of Example 4 as Comparative Example

| Product | Theoretical Functionality | Mn GPC | Mw GPC | n | Equivalent Mn Per Acrylate |
| --- | --- | --- | --- | --- | --- |
| Oligomer 3 | 2 | 2644 | 3634 | 1 | 1322 |

The oligomer 3 has a theoretical average in number-functionality of 2, a weight average molecular weight (GPC Mw) of 3,600 g/mol, a number average molecular weight (GPC Mn) of about 2,600 g/mol and an equivalent molecular weight per acrylate of about 1,300.

Table 11 below lists the ingredients and their weight % (wt %) values for coating composition of Example 4 as comparative example. The oligomer 3 (e.g., urethane acrylate without any diluent) is contained in a wt % at about 42.5%. Cycloaliphatic methacrylates as defined according to diluent b), including isobornyl acrylate, tricyclodecane dimethanol diacrylate and 3,3,5-trimethylcyclohexyl acrylate are contained in a wt % at about 52.5%. The photo-initiator is contained in a wt % at about 5%.

TABLE 11

Ingredients of coating composition of Example 4 as comparative example

| | |
| --- | --- |
| Oligomer 3 (without any diluent) | 42.5 wt % |
| Isobonyl Acrylate | 7.5 wt % |
| Tricyclodecane dimethanol diacrylate | 25 wt % |
| 3,3,5-Trimethycyclohexyl | 20 wt % |
| Photoinitiator | 5 wt % |

Table 12 below lists the properties for the cured coating composition of Example 4, as a comparative example (outside the covering of present invention), with respect to removability in acetone. As can been seen, the cured coating of Example 4 (comparative) shows poor removability in acetone for 5 minutes or less and is not completely removed until 15 minutes.

TABLE 12

Soak Off Properties of the cured coating composition of Example 4, as comparative example

| Soak off, after being soaked in acetone for | Example 4 |
| --- | --- |
| 5 minutes | 0% |
| 15 minutes | 100% |

Furthermore, industrial standard commercial products Gelcolor supplied by Coty Inc. and Gelish supplied by Hand & Nail Harmony are used in comparison to Examples 1-4. Table 13 below lists the hardness and gloss Gelcolor and Gelish top coatings.

TABLE 13

Properties of OPI and Gelish nail Top Coatings

| | Gelcolor nail top coat | Gelish nail top coat |
| --- | --- | --- |
| Pencil Hardness | F | F |
| Shine Gloss values | | |
| 20° | 71.7 | 63.8 |
| 60° | 108 | 104 |
| 85° | 93.1 | 95.7 |

As can be seen, the Gelcolor and Gelish nail top coatings, while suitably hard, do not perform as well as Examples 1-3 with respect to gloss.

Table 14 below lists the properties for Gelcolor and Gelish coatings (as used with base, color and/or top coatings) with respect to removability in acetone. As can been seen, Gelcolor and Gelish coatings shows poor removability in acetone for 5 minutes or less and are not completely removed until 30 minutes.

TABLE 14

Soak Off Properties of Gelcolor and Gelish Coatings

| | OPI, Gelcolor base coat, color layer and top coat | Gelish base coat and top coat |
|---|---|---|
| Soak off, after being soaked in acetone for | F | F |
| 5 mins | 15% | 5% |
| 15 mins | 80% | 80% |
| 30 mins | 100% | 100% |
| Adhesion on artificial nails | 4 | 4 |

Compared with the industry standard OPI soak off products (which typically include a base coat, color layer and three top coat layers) and Gelish soak off products (which typically include a base coat and two top coat layers), the soak off properties of Examples 1-3 (invention) were much shorter for complete removal.

Coating compositions of examples 1 to 3 (invention) have viscosity of 2000 cps to 9000 cP (mPa·s) at room temperature. They are applicable to artificial nails by brush. After curing under Gelish LED lamp or CND UV lamp, the applied coating has a very high gloss. After wiping the surface by 99 wt % isopropanol, the coating still remain high gloss. After sitting under light at ambient temperature, the coating become shiner and shiner.

When the word "about" is used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages.

It will now be apparent that a new, improved and non-obvious electronic aerosol generating article has been described in this specification with sufficient particularity as to be understood by one of ordinary skill in the art. Moreover, it will be apparent to those skilled in the art that modifications, variations, substitutions and equivalents exist for features of the electronic aerosol generating article which do not materially depart from the spirit and scope of the embodiments disclosed herein. Accordingly, it is expressly intended that all such modifications, variations, substitutions and equivalents which fall within the spirit and scope of the invention as defined by the appended claims shall be embraced by the appended claims.

The invention claimed is:

1. A coating composition comprising:
   a) at least one urethane (meth)acrylate oligomer of formula (I)

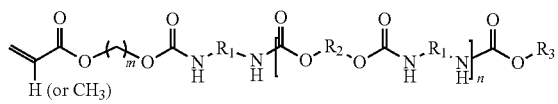

(I)

wherein $2 \leq n \leq 20$ and $2 \leq m \leq 4$;
   R1 is selected from the group consisting of alkylene, cycloalkylene, arylene, arylkylene and combinations thereof;
   R2 is selected from the group consisting of alkylenes, cycloalkylenes and arylalkylenes;
   R3 comprises a moiety of —R4-OH, wherein the oligomer a) has a mean free OH value of about 2 mg KOH/g to about 50 mg KOH/g and R3 comprises a moiety of —R5-(meth)acryloyl;
   R4 and R5 being a bivalent radical selected from the group consisting of alkylenes, cycloalkylenes and arylalkylenes, with R4 and R5 being identical or different from each other; and
   wherein the at least one urethane (meth)acrylate oligomer has a number average molecular weight Mn measured by GPC, of from about 2,000 g/mol to about 50,000 g/mol and wherein the at least one urethane (meth) acrylate oligomer a) has an average in number-functionality of from about 1.1 to about 1.9 (meth)acrylates;
   b) at least one cycloaliphatic (meth)acrylate; and
   c) optionally, at least one allylic compound from allylic monomers and/or oligomers bearing at least one allylic group,
   d) optionally, at least one component selected from the group of additives consisting of an adhesion promoter, a photo-initiator, a thiol compound, a pigment, a dye, a plasticizer and combinations thereof.

2. The coating composition of claim 1, wherein the said composition is curable.

3. The coating composition of claim 1, wherein the coating composition comprises less than 1% by weight of non-reactive solvent and less than 1% by weight of non-reactive, solvent-dissolvable polymer.

4. The coating composition of claim 1, wherein the coating composition comprises an adhesion promoter that includes one or more functional groups selected from the group consisting of hydroxyl groups, carboxylic acids, phosphoric acids and combinations thereof.

5. The coating composition of claim 4, wherein the adhesion promoter is selected from the group consisting of hydroxylethyl (meth)acrylate, hydroxylpropyl (meth)acrylates, pyromellitic dianhydride dialkyl(meth)acrylate, phathalic acid monoalkyl (meth)acrylates, succinic acid monoalkyl (meth)acrylates, phosphoric acid or phosphoric ester functional (meth)acrylates and carboxylic acid functional (meth)acrylates and combinations thereof.

6. The coating composition of claim 1, wherein said composition further comprises an allylic compound c) bearing at least one allylic group and optionally a metal ion catalyst.

7. The coating composition of claim 2, wherein the coating composition comprises a photo-initiator selected from the group consisting of α-hydroxyketones, phenylglyoxylates, benzyldimethylketals, α-aminoketones, monoacyl phosphines, bis-acyl phosphines, phosphine oxides and metallocenes and combinations thereof.

8. The coating composition of claim 1, wherein the cycloaliphatic (meth)acrylate b) comprises a (meth)acrylate monomer bearing at least one mono-, bi- or tri-cyclic group.

9. The coating composition of claim 1, wherein the cycloaliphatic (meth)acrylate b) is selected from the group consisting of 3,3,5-Trimethycyclohexyl acrylate, tricyclodecane dimethanol (meth)acrylate, (alkoxylated) isobornyl (meth)acrylate, (alkoxylated) isophoryl (meth)acrylate, (alkoxylated) trimethylolpropane cyclic formal (meth)acrylate, (alkoxylated) tertiobutylcyclohexyl (meth)acrylate, (alkoxylated) tetrahydrofurfuryl (meth)acrylate, (alkoxylated) dicyclopentadiene (alkoxylated) (meth)acrylate, (alkoxylated) tricyclodecane dimethanol (meth)acrylate, (alkoxylated) cyclohexane dimethanol (meth)acrylate, (alkoxylated) (di)cyclopentenyl (meth)acrylate, (alkoxylated) cyclohexyl (meth)acrylate, (alkoxylated) norbornyl (meth)acrylate, (alkoxylated) (meth)acrylate based on rosin (hydroxyalkyl (meth)acrylate ester with abietic acid) and combinations thereof.

10. The coating composition of claim 1, wherein the cycloaliphatic (meth)acrylate b) is present from 20% to about 80% by weight of the coating composition.

11. The coating composition of claim 1, wherein the cured coating has two phases, a soft phase which has a Tg between −50° C. and 0° C. and a hard phase which has a Tg between 60° C. and 120° C.

12. The coating composition of claim 1, wherein the at least one urethane (meth)acrylate oligomer a) has a molecular weight Mn of from about 3,000 g/mol to about 25,000 g/mol.

13. The coating composition of claim 1, wherein 3≤n≤10.

14. A coating composition comprising:
a) at least one urethane (meth)acrylate oligomer of formula (I)

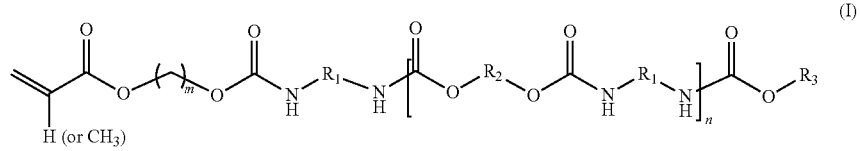

wherein 2≤n≤20 and 2≤m≤4;
R1 is selected from the group consisting of alkylene, cycloalkylene, arylene, aralkylene and combinations thereof;
R2 is selected from the group consisting of alkylenes, cycloalkylenes, arylalkylenes and combinations thereof;
R3 comprises a moiety of —R4-OH, wherein the oligomer a) has a mean free OH value of about 2 mg KOH/g to about 50 mg KOH/g and R3 comprises a moiety of —R5-(meth)acryloyl;
R4 and R5 being a bivalent radical selected from the group consisting of alkylenes, cycloalkylenes and arylalkylenes, with R4 and R5 being identical or different from each other; and
wherein the at least one urethane (meth)acrylate oligomer has a molecular weight of from about 2,000 g/mol to about 50,000 g/mol and wherein the at least one urethane (meth)acrylate oligomer
a) has an average in number-functionality of from about 1.1 to about 1.9 (meth)acrylates;
b) at least one cycloaliphatic (meth)acrylate; and
c) optionally, at least one allylic compound from allylic monomers and/or oligomers bearing at least one allylic group,
d) optionally, at least one component selected from the group consisting of an adhesion promoter, a photoinitiator, a pigment, a dye, a plasticizer and combinations thereof; and wherein the coating composition comprises less than 1% by weight of non-reactive solvent and less than 1% by weight of non-reactive, solvent-dissolvable polymer and the coating after curing has two phases, a soft phase which has a Tg between −50° C. and 0° C. and a hard phase which has a Tg between 60° C. and 120° C.

15. The coating composition of claim 14, wherein the composition is curable.

16. The coating composition of claim 14, wherein said composition comprises an allylic compound c) bearing at least one allylic group.

17. A method of coating a nail with the composition of claim 1, comprising:
applying the coating composition to a nail and hardening (curing) the coating composition.

18. The method of claim 17, wherein the hardening (curing) comprises curing the coating composition by exposure to radiant (radiation) energy, by exposure to electron beam radiation, by exposure to heat, by exposure to chemicals or combinations thereof.

19. The coating composition of claim 1, wherein it is suitable for nail cosmetics.

20. The coating composition of claim 1, suitable for nail coatings.

21. A coating resulting from curing (hardening) the coating composition of claim 1.

22. The coating of claim 21, wherein it is a cosmetic or a nail coating.

* * * * *